(12) United States Patent
Lentner et al.

(10) Patent No.: US 8,983,018 B2
(45) Date of Patent: Mar. 17, 2015

(54) METHOD AND APPARATUS FOR A RISER PIPE REPAIR WITH COMPRESSION

(75) Inventors: Bruce J. Lentner, Wilmington, NC (US); Michael S. Defilippis, Wilmington, NC (US); Khaled M. Ewida, Garland, TX (US); Robin D. Sprague, Wilmington, NC (US); Luke A. Davis, Salem, VA (US)

(73) Assignee: GE-Hitachi Nuclear Energy Americas LLC, Wilmington, NC (US)

( * ) Notice: Subject to any disclaimer, the term of this patent is extended or adjusted under 35 U.S.C. 154(b) by 855 days.

(21) Appl. No.: 12/969,845

(22) Filed: Dec. 16, 2010

(65) Prior Publication Data

US 2012/0155598 A1 Jun. 21, 2012

(51) Int. Cl.
| | | |
|---|---|---|
| G21C 3/56 | (2006.01) |
| G21C 15/25 | (2006.01) |
| G21C 17/017 | (2006.01) |
| F22B 1/14 | (2006.01) |
| G01N 1/14 | (2006.01) |

(52) U.S. Cl.
CPC .................. *G21C 15/25* (2013.01); *F22B 1/143* (2013.01); *G01N 1/14* (2013.01); *G21C 17/017* (2013.01); *Y02E 30/31* (2013.01)
USPC .......................................................... 376/392

(58) Field of Classification Search
CPC ...... G21C 15/25; G21C 17/017; Y02E 30/31; F22B 1/143; G01N 1/14
USPC .......................................................... 376/392
See application file for complete search history.

(56) References Cited

U.S. PATENT DOCUMENTS

| 4,653,782 A * | 3/1987 | Munday .......................... 285/373 |
| 4,774,752 A * | 10/1988 | Cooper, Jr. et al. .......... 29/426.4 |
| 6,086,120 A | 7/2000 | Deaver et al. |
| 7,272,204 B2 | 9/2007 | Jensen |
| 8,038,174 B2 | 10/2011 | Jensen |
| 2008/0205578 A1 * | 8/2008 | Abura et al. ................... 376/372 |

(Continued)

FOREIGN PATENT DOCUMENTS

| GB | 538 730 A | 8/1941 |
| GB | 2197420 A * | 5/1988 |

(Continued)

OTHER PUBLICATIONS

Search Report issued in connection with EP Patent Application No. 11192596.2, Apr. 17, 2012.

(Continued)

*Primary Examiner* — Frank J McGue
(74) *Attorney, Agent, or Firm* — Harness, Dickey & Pierce, P.L.C.

(57) ABSTRACT

A method and apparatus for repairing and/or reinforcing a Boiling Water Reactor (BWR) jet pump riser pipe. The repair includes attaching two collars to the riser pipe using match drilling to drill holes through the collars and the riser pipe and plugging the holes with expandable plugs. Support columns are attached to the collars. Brace supports are slideably attached to the support columns. Gaps between each brace support and its respective collar are then narrowed as ratchet bolts may apply a force that pulls downward on an upper collar and pulls upward on a lower collar, thereby exerting a compression force on the riser pipe. A clamp assembly may also be located between the two collars that applies a hoop force on the riser pipe.

21 Claims, 17 Drawing Sheets

(56) References Cited

U.S. PATENT DOCUMENTS

| | | |
|---|---|---|
| 2009/0127854 A1 | 5/2009 | Jensen |
| 2010/0032938 A1 | 2/2010 | Jensen |
| 2012/0155599 A1* | 6/2012 | Sprague et al. ............... 376/392 |

FOREIGN PATENT DOCUMENTS

| | | |
|---|---|---|
| JP | 61-211508 | 9/1986 |
| JP | H11264400 A | 9/1999 |
| JP | 2006071638 A | 3/2006 |
| JP | 2008046020 A | 2/2008 |
| JP | 2010044068 A | 2/2010 |
| JP | 2012127960 A | 7/2012 |

OTHER PUBLICATIONS

Notice of Allowance dated May 27, 2014 issued in corresponding JP Application No. 2011-272887 (with translation).

Unofficial English translation of a JP Office Action dated Feb. 4, 2014, issued in connection with corresponding JP Patent Application No. 2011-272887.

* cited by examiner

METHOD AND APPARATUS FOR A RISER PIPE REPAIR WITH COMPRESSION

BACKGROUND OF THE INVENTION

1. Field of the Invention

Example embodiments relate generally to nuclear reactors, and more particularly to a method and apparatus for a Boiling Water Reactor (BWR) jet pump riser pipe repair with compression that provides hoop and axial strength reinforcement to a riser pipe. The repair may be used to repair a cracked riser pipe, or it may be used as a preventative means of supporting the riser pipe prior to the formation of a crack.

2. Related Art

A reactor pressure vessel (RPV) of a boiling water reactor (BWR) typically has a generally cylindrical shape and is closed at both ends (for example by a bottom head and a removable top head). A top guide typically is spaced above a core plate within the RPV. A core shroud, or shroud, typically surrounds the core and is supported by a shroud support structure. Particularly, the shroud has a generally cylindrical shape and surrounds both the core plate and the top guide. There is a space or annulus between the cylindrical reactor pressure vessel and the cylindrically shaped shroud.

In a BWR, a jet pump assembly is positioned within the shroud annulus to provide reactor core water flow to the reactor. The upper portion of the jet pump assembly, known as the inlet mixer, receives water from a large riser pipe and discharges the reactor water to two diffusers which inject the water into the reactor. The riser pipe is generally supported by a riser brace and the RPV penetration to stabilize the pipe from system vibration and pressure fluctuations during operation of the jet pump assembly. System vibration and pressure fluctuations may ultimately cause minute cracks to form in the riser pipe. The cracks may become exacerbated by continual use of the jet pump assembly. Conventionally, costly repair may be required to replace damaged sections of the riser pipe.

SUMMARY OF INVENTION

Example embodiments provide a method and an apparatus for providing a repair offering hoop and axial strength reinforcement to the riser pipe at or near the location of the riser brace of a BWR jet pump assembly. Specifically, a collar assembly may function as a riser brace bracket that provides axial strength to compress the riser pipe in a lengthwise direction. Furthermore, a clamp assembly may offer hoop strength to reinforce the riser pipe and resist forces exerted on the pipe in a radial direction. The collar assembly may be stabilized by being attached directly to the riser brace, thereby also reinforcing and/or repairing welds between the riser pipe and the riser brace. The collar assembly and the clamp assembly may be one integral component or separate components that may be used in conjunction with each other providing overall reinforcement and/or repair of the riser pipe.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION

Figure 1:
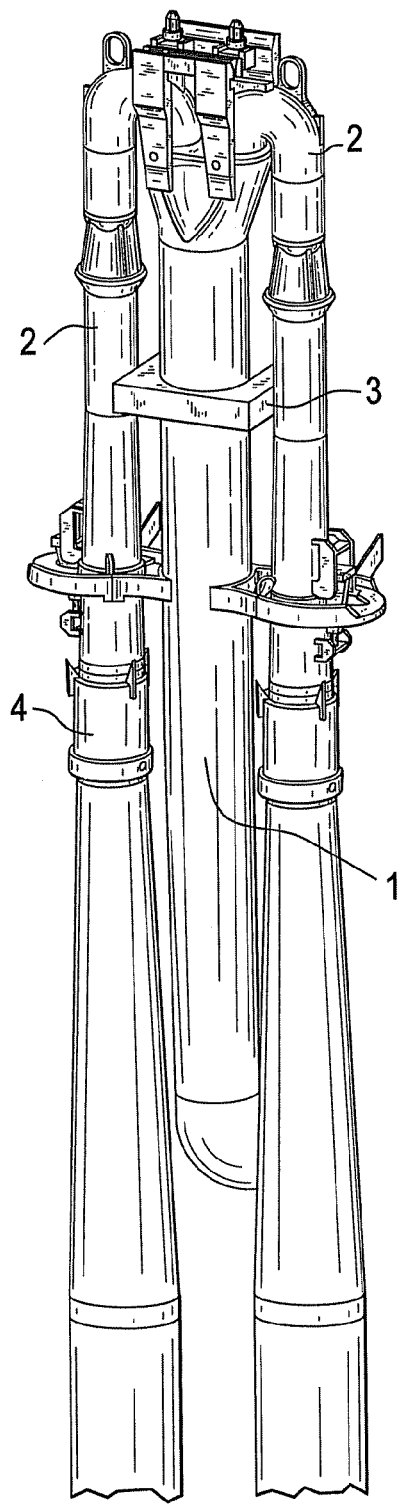
FIG. 1 is a perspective view of a conventional boiling water reactor (BWR) jet pump assembly.

Detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It will be understood that, although the tee ins first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it may be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between", "adjacent" versus "directly adjacent", etc.).

The terminology used herein is for the purpose of describing particular embodiments only and is not intended to be limiting of example embodiments. As used herein, the singular fowls "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Referring to FIG. 1, a perspective view of a conventional Nuclear Boiling Water Reactor (BWR) jet pump assembly is depicted. The jet pump assembly includes a riser pipe 1 that provides water to two inlet mixers 2. The inlet mixers 2 discharge water to the reactor through respective diffusers 4. Notice that riser pipe 1 is conventionally stabilized via riser brace 3 and the RPV penetration.

Figure 2:
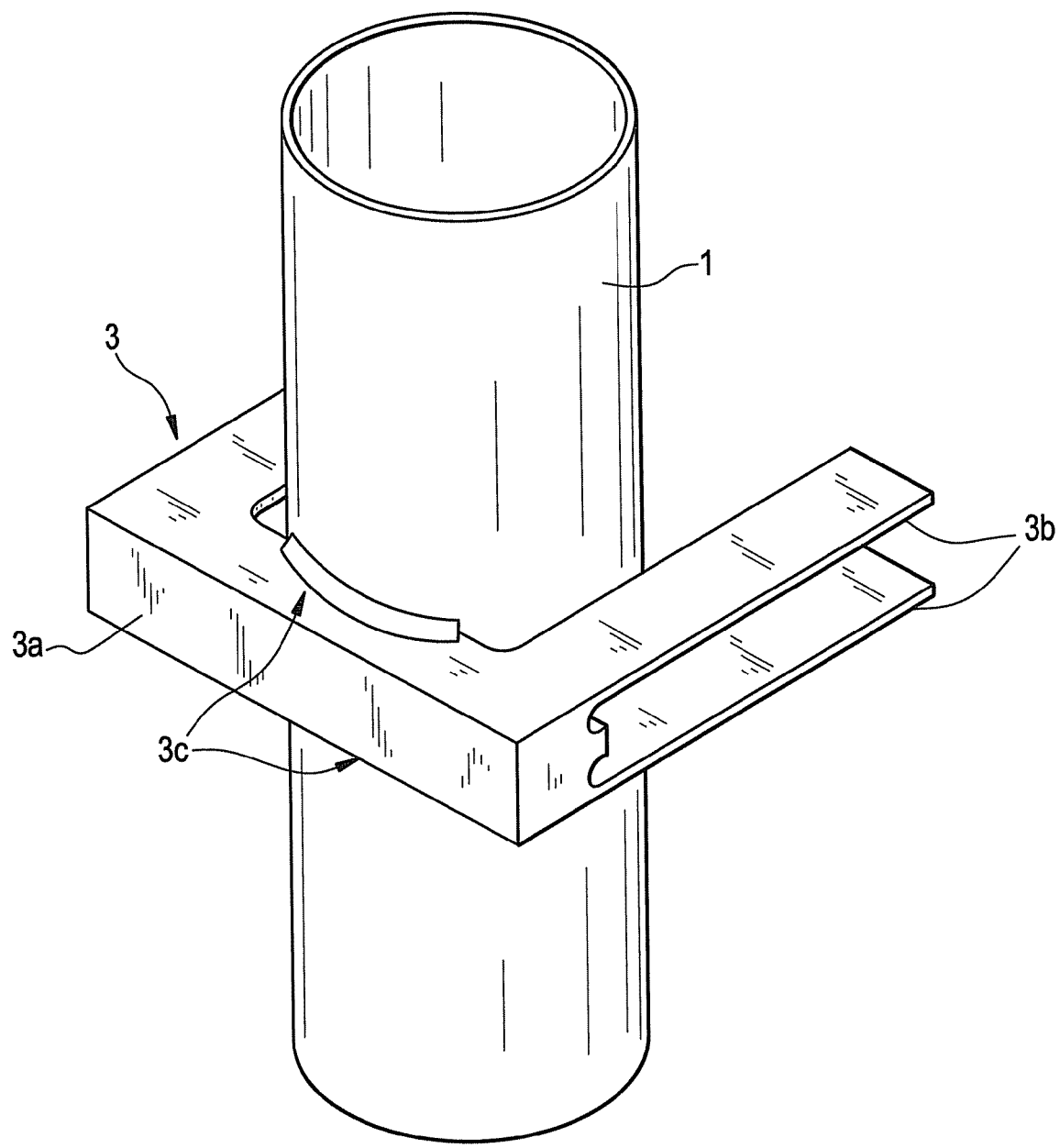
FIG. 2 is a simplified depiction of a conventional weld between a riser pipe and a riser brace yoke of a conventional BWR jet pump assembly.

FIG. 2 is a simplified depiction of a conventional weld 3c between a riser pipe 1 and a riser brace yoke 3a of a conventional BWR jet pump assembly. The weld 3c may be formed at both the top and bottom of the riser brace yoke, to secure the riser brace to the riser pipe 1. The welds 3c may degrade over time as system vibration and pressure fluctuations strain the welds 3c.

Figure 3:
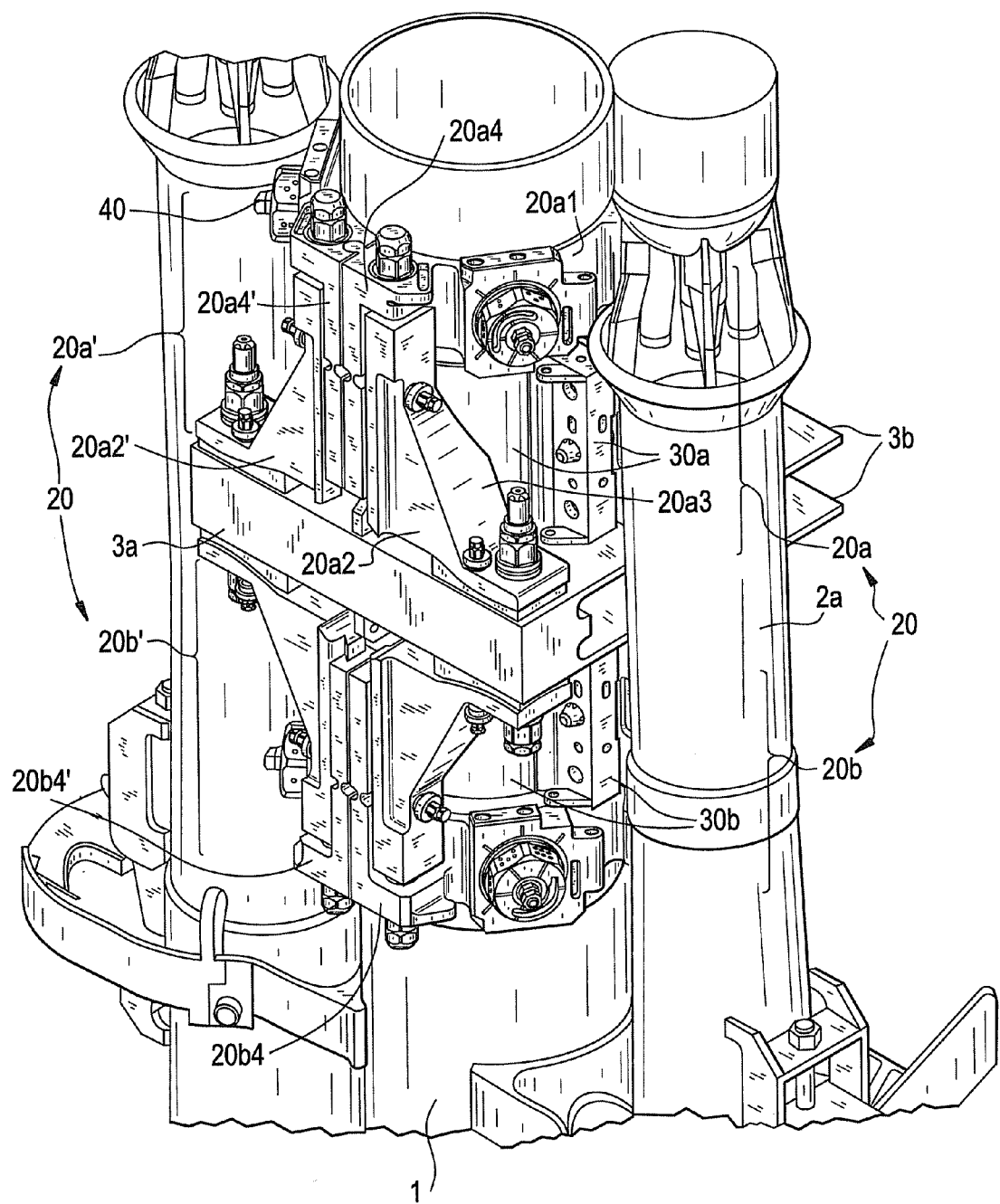
FIG. 3 is a detailed view of a riser pipe repair with compression installed on a BWR jet pump assembly in accordance with an example embodiment.

FIG. 3 is a detailed view of a riser pipe repair with compression 20 installed on a BWR jet pump assembly in accordance with an example embodiment. The repair 20 hardware may be located on the riser pipe, above and below the riser brace 3. Moving from approximately the top of the figure to the bottom of the figure, the upper portion of the riser pipe repair may generally include two major portions, a right upper collar assembly 20a and a left upper collar assembly 20a'. The right upper collar assembly 20a may include an upper collar 20a1 that may be attached to riser pipe 1 above the riser brace 3. The left upper collar assembly 20a' may include a similar upper collar 20a1', shown best in FIG. 6. One or more plug assemblies 40 may be used to firmly secure the upper collar 20a1 (and 20a1') to the pipe 1. The upper collar 20a1 (and 20a1') may be attached to the riser brace yoke 3a (the yoke 3a is the front of the riser brace 3) by major components that include inner collar support columns 20a4'/20a4 and brace supports 20a2'/20a2 that act to pull the upper collars 20a1'/20a1 down to place a compression force on the riser pipe 1. An upper clamp assembly 30a may also be provided around the riser pipe 1 and above the riser brace 3 (shown more clearly in FIG. 9) that applies a hoop strength force to the riser pipe 1.

Below the riser brace 3, a lower clamp assembly 30b may be provided (again, shown in more detail in FIG. 9). A lower collar assembly (left and right side) 20b'/20b may include a lower collar 20b1' (shown best in FIG. 8)/20b1 that may also be attached to the riser pipe 1 via plug assemblies 40. The lower collar 20b1'/20b1 may be connected to the riser brace yoke 3a via inner collar support columns 20b4'/20b4 and lower brace supports 20b2'/20b2 that act to pull the lower collar 20b1'/20b1 upward to place a compression force on riser pipe 1. The riser pipe repair with compression collectively includes assemblies 20a, 20a', 20b and 20b'.

Figure 4:
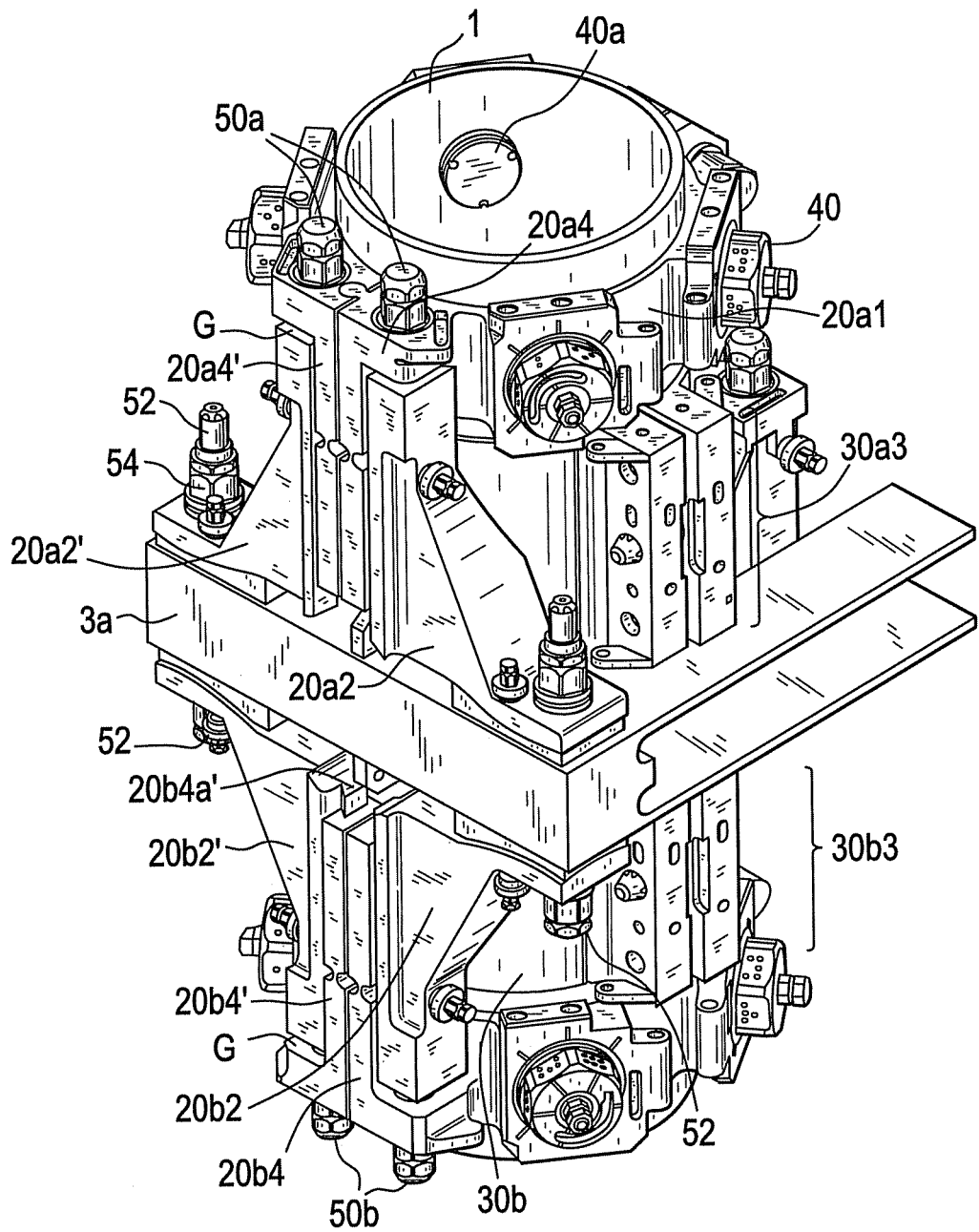
FIG. 4 is a detailed view of a riser pipe repair with compression installed on a riser pipe in accordance with an example embodiment.

FIG. 4 is a detailed view of a riser pipe repair with compression installed on a riser pipe 1 in accordance with an example embodiment. Notice that crimp nuts 54 and yoke bolts 52 may be used in upper and lower assemblies to securely fasten upper brace supports 20a2'/20a2 and lower brace supports 20b2'/20b2 to the riser brace yoke 3a. Spherical washers may be used underneath the yoke bolts 52 (i.e., the washer may be located between bolt 52 and brace support 20a2', for instance) and underneath crimp nut 54 (i.e., the washer may be located between nut 54 and brace support 20b2, for instance). The spherical washers may provide an additional tolerance, in the event that either the upper brace supports 20a2/20a2' or the lower brace supports 20b2/20b2' are not entirely perpendicularly aligned with riser brace yoke 3a. Inner ratchet bolts 50a/50b are used to pull upper collar 20a1'/20a1 and lower collar 20b1'/20b1 toward the riser brace yoke 3a. Specifically, brace supports 20b2' may be provided with a male dovetail portion 20b4a' that may mate with a female dovetail portion 20b4b' allowing inner collar support column 20b4' to move closer to brace yoke 3a as inner ratchet bolt 50b is tightened, thereby causing gap G to narrow as yoke bolts 52 place a compression force on the riser pipe 1. Alternative to using a dovetail, an interlock or some other means of slideably attaching the support column 20b4' and brace support 20b2' may instead be used. While example embodiments show a dovetail connection 20b4a'/20b4b' between the brace supports 20b2' and the inner collar support column 20b4', it is to be understood that other means of allowing the brace supports 20b2' and the inner collar support column 20b4' to remain connected as they slide between each other may also be used.

Note that each plug assembly 40 may be attached to the riser pipe by using match drilling to penetrate holes clear through the riser pipe 1 and respective upper collar assemblies 20a/20a' and lower collar assemblies 20b/20b'. An expandable plug assembly including an expandable section 40a may then ensure that each of the upper and lower collars 20a1'/20a1 and 20b1'/20b1 may be securely fastened with significant strength to then allow ratchet bolts 50a/50b to put the requisite compression force on riser pipe 1. The expandable plug assembly 40 may for instance be the expandable plug that is disclosed in U.S. patent application Ser. No. (unknown), filed concurrently with this application and entitled "METHOD AND APPARATUS FOR AN EXPANDING SPLIT BUSHING PIPE PLUG ASSEMBLY," the entire contents of which are hereby incorporated by reference. The compression force may be applied to the riser pipe 1 to reduce and/or prevent cracking that may occur in the riser pipe between the upper and lower collars 20a1'/20a1 and 20b1'/20b1.

Figure 9:
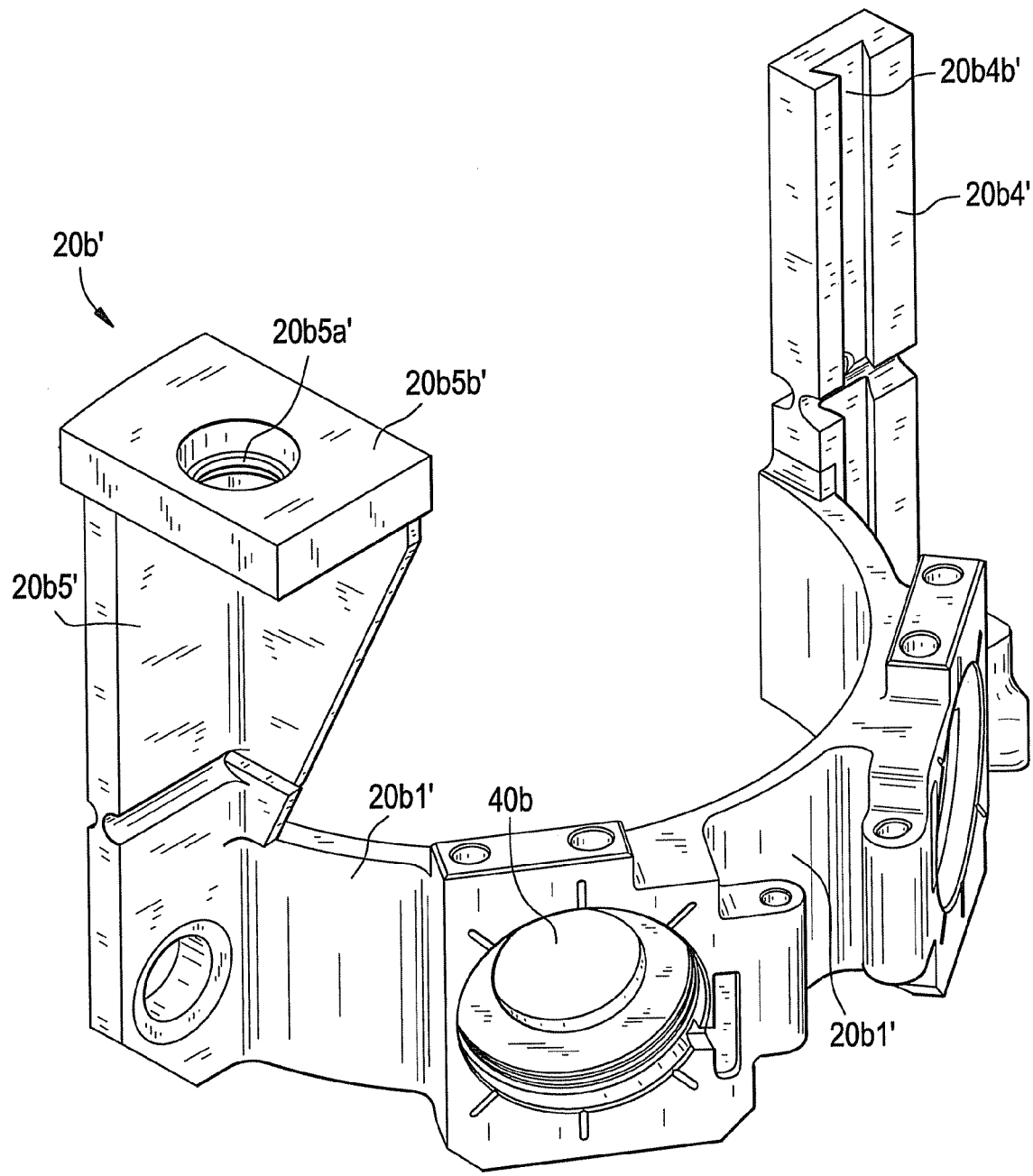
FIG. 9 is a detailed view of a lower collar assembly (left side), in accordance with an example embodiment.
Figure 10:
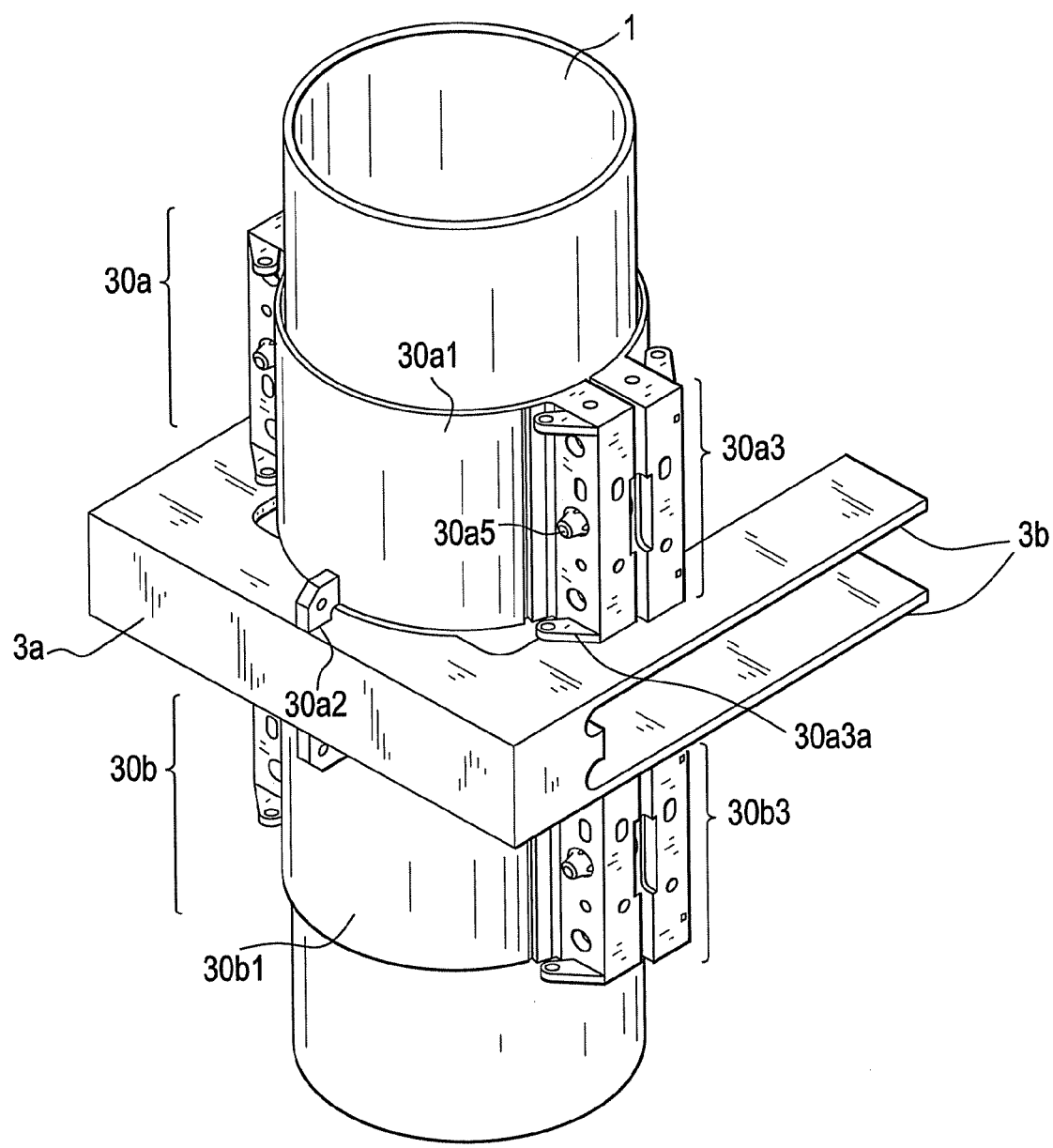
FIG. 10 is a detailed view of a clamp assembly installed above and below a riser brace on a riser pipe, in accordance with an example embodiment.

FIG. 4 depicts the upper and lower clamp assemblies 30a/30b in more detail, as the upper and lower mating fixtures 30a3/30b3 can be seen in somewhat more detail (see FIGS. 9-10 for more detail of the clamp assemblies 30a/30b).

Figure 5:
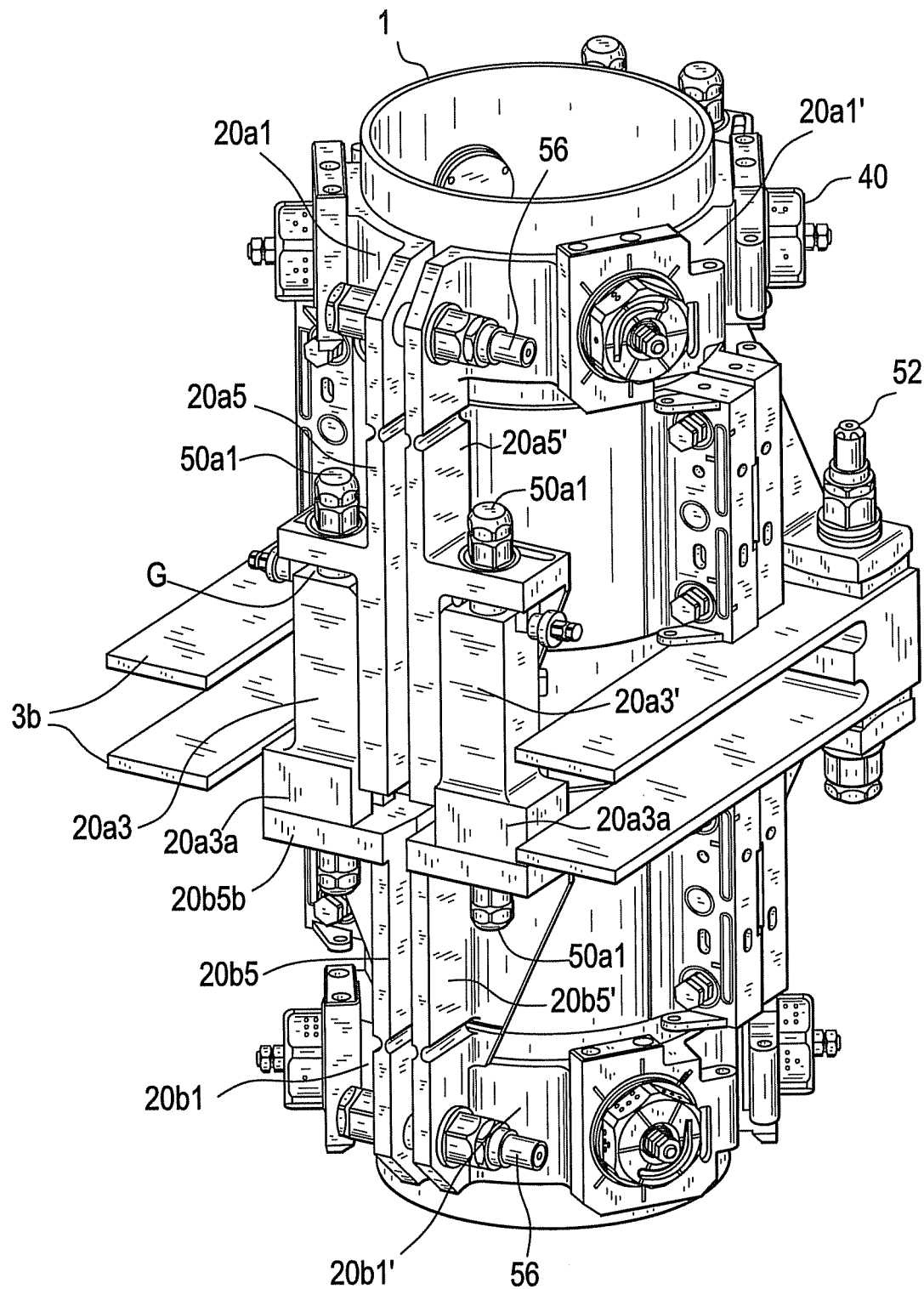
FIG. 5 is a detailed view of a riser pipe repair with compressions installed on a riser pipe and shown in a reverse angle, in accordance with an example embodiment.

FIG. 5 is a detailed view of a riser pipe repair with compressions installed on a riser pipe 1 and shown in a reverse angle, in accordance with an example embodiment. Note that FIG. 5 shows the left upper collar 20a1' and the left lower collar 20b1' which could not clearly be seen in FIG. 4. These collars also may have plug assemblies 40 that may be used to secure the collars 20a1'/20b1' to the riser pipe 1. On this side of the riser pipe 1, ends of the riser brace leaves 3b attach directly to the shroud wall such that no yoke exists as an attachment point for the upper and lower collars (20a1'/20b1'). Therefore, upper outer support columns (20a5/20a5') may be provided to attach to outer lower support columns (20b5/20b5') via outer ratchet bolts 50a1. Specifically, brace supports 20a3/20a3' are provided on the outer collar support columns 20a5/20a5' (notice gap G between brace support 20a3 and collar support column 20a5). The brace support feet 20a3a/20a3a' of the brace supports 20a3/20a3' of the upper collar assemblies contact outer collar support column feet 20b5b/20b5b' of the outer collar support columns 20b5/20b5' of the lower collar assemblies. As outer ratchet bolts are tightened, gap G closes as riser pipe 1 is placed into compression as the upper collars 20a1/20a1' and the lower collars 20b1/20b1' are pulled toward each other. Collar bolts 56 may also be provided to penetrate the outer collar support columns (upper assemblies) 20a5/20a5' and the outer collar support columns (lower assemblies) 20b5/20b5' to further secure the collars to each other as well as the riser pipe 1.

Figure 6:
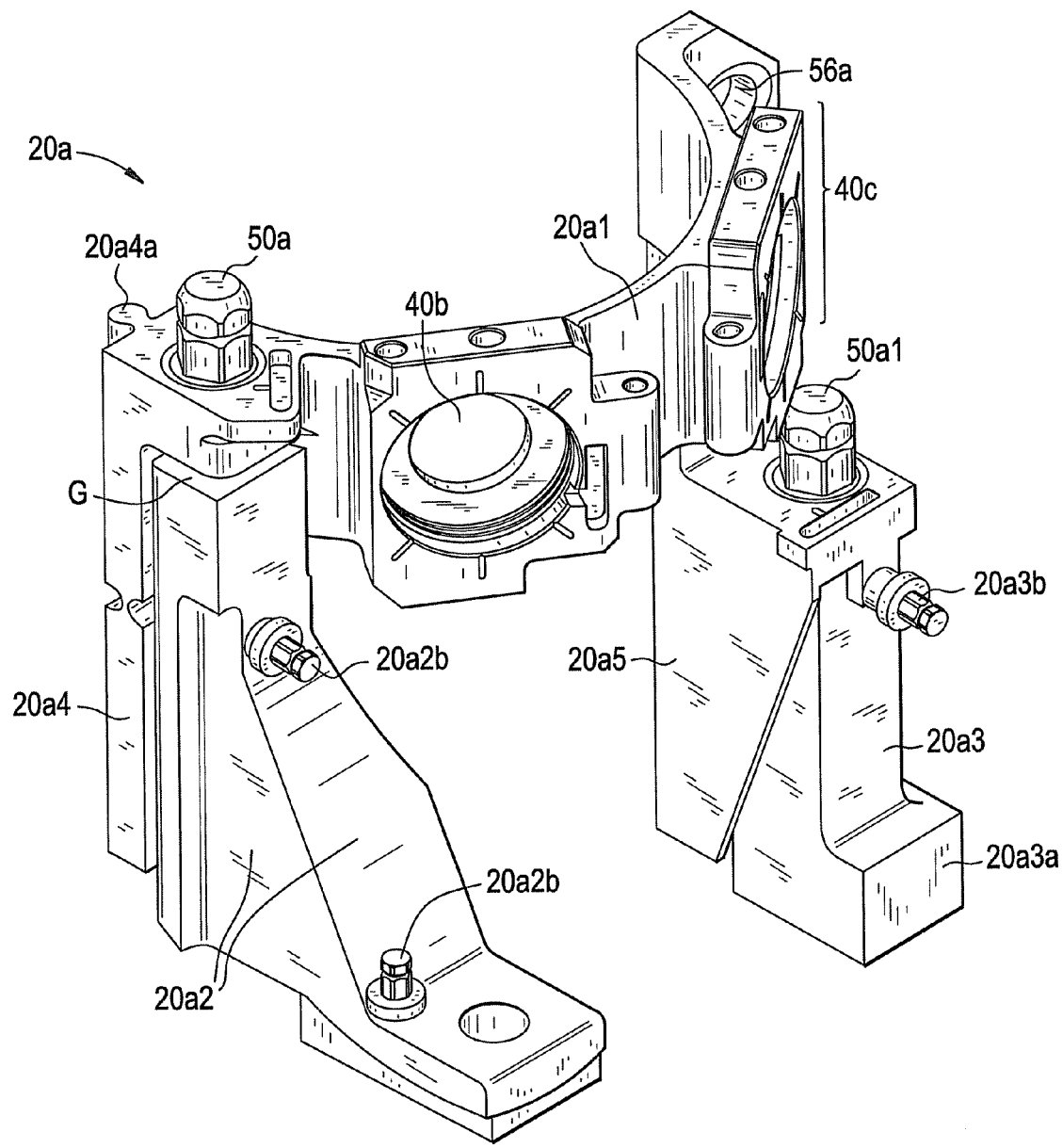
FIG. 6 is a detailed view of an upper collar assembly (right side), in accordance with an example embodiment.

FIG. 6 is a detailed view of an upper collar assembly (right side) 20a, in accordance with an example embodiment. Note that much of the following discussion of collar assembly 20a applies to the other three collar assemblies (20a', 20b and 20b'), as each of the four collars contain some common features. Note that upper collar assembly 20a may include a C-shaped half collar 20a1 with undersized collar holes 40b that may be used to secure collar 20a1 to the riser pipe 1 (collar holes 40b may be filled with an expandable plug assembly 40, shown in FIGS. 3-5, that may penetrate the riser pipe 1 and collar 20a1 to firmly attach the collar assembly 20a to riser pipe 1). Plug pads 40c may reinforce each collar hole 40b for added strength and to provide a working surface for match drilling the collar hole 40b and the hole that penetrates the riser pipe 1 itself. Male interlocks 20a4a may be provided on inner collar support column 20a4 to mate with female slots 20a4b' (shown in FIG. 7), to interlock the two upper collar assemblies 20a/20a'. Alternatively to using the interlock, dovetails or other means of securely attaching support column 20a4 to support column 20a4' (shown in FIG. 7) may instead be used.

Collar bolt holes 56a may be provided on outer collar support column 20a5 to attach the outer end of each of the upper collar assemblies 20a/20a' to each other. Notice gap G between inner collar support column 20a4 and brace support 20a2. Gap G decreases when inner ratchet bolt 50a is tightened when collar assembly 20a is in operation and attached to the riser pipe 1. Temporary alignment bolts 20a2b may be provided to temporarily hold brace support 20a2 to collar support column 20a4 and brace support foot pad 20a2a1 prior to collar assembly 20a being installed on the equipment in the field. Brace support foot 20a2a may be provided with a spherical (convex) seat that mates with brace support foot pad 20a2a1 that also has a spherical surface (concave). The spherical nature of the support foot 20a2a and foot pad 20a2a1 provides a tolerance in the event that inner support columns 20a4/20a4' are not exactly perpendicular with yoke 3a (see FIG. 3) upon installation (i.e., brace support 20a2 may swivel, and provide a tolerance to some degree, on foot pad 20a2a1). Hole 20a2a2 may be provided through brace support foot 20a2a and foot pad 20a2a1 to allow yoke bolt 52 (shown in FIG. 4) to secure brace support 20a2 to riser brace yoke 3a (as shown in at least FIG. 4).

Outer collar support column 20a5 may house brace bracket 20a3. Temporary alignment pin 20a3b may be used to temporarily hold brace bracket on collar support column 20a5, prior to installation. Brace bracket foot 20a3a connects to outer collar support column foot 20b5b via outer ratchet bolt 50a1 (as shown for instance in FIG. 5). Outer ratchet bolt may be tightened to close gap G (see in FIG. 5) in order to pull upper collars 20a1/20a1' downward and pull lower collars 20b1/20b1' upward to then compress the riser pipe 1.

Figure 6A:
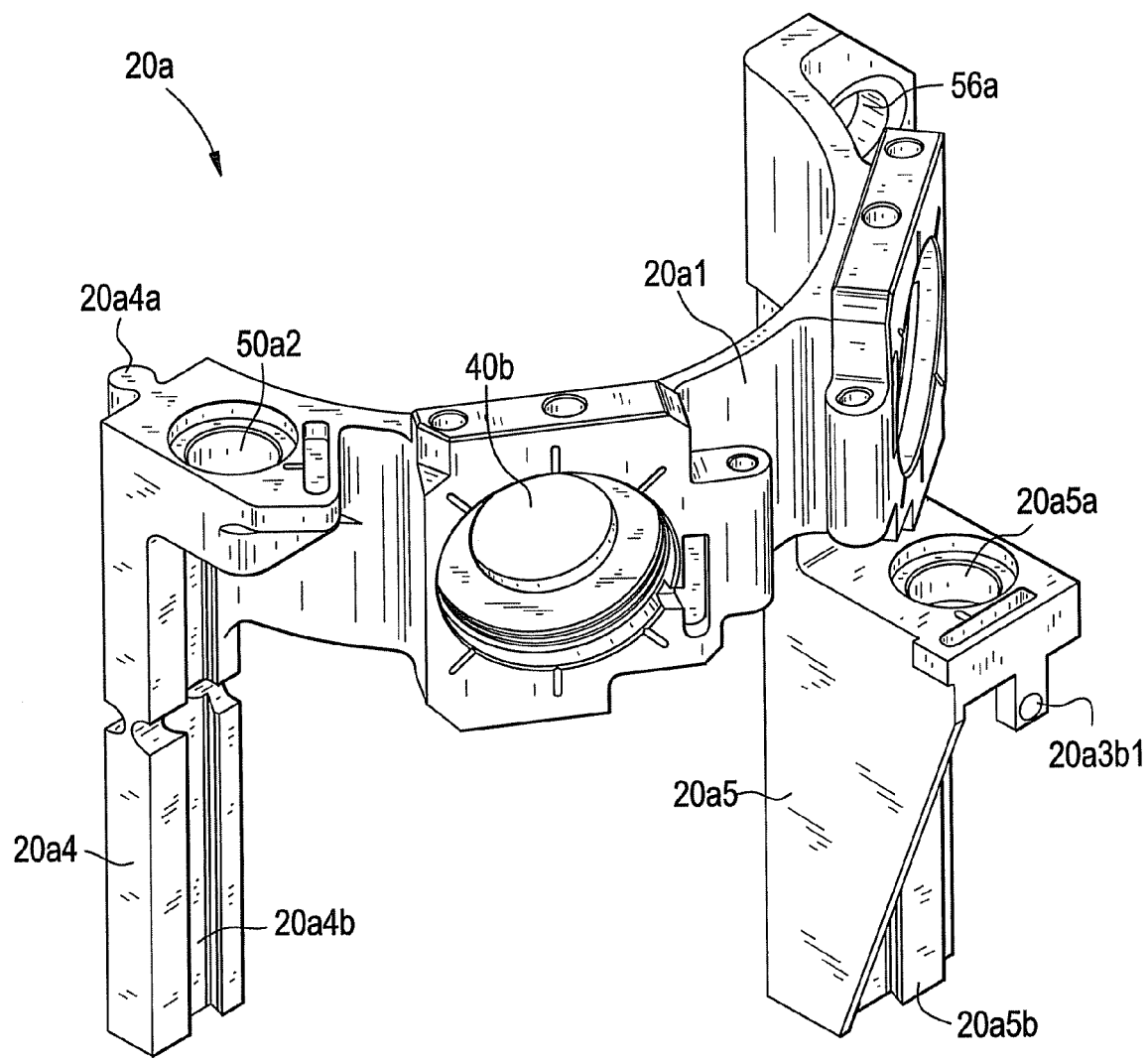
FIG. 6A is a detailed view of an upper collar assembly (right side) component (without additional hardware), in accordance with an example embodiment.

FIG. 6A is a detailed view of an upper collar assembly (right side) 20a component (without additional hardware), in accordance with an example embodiment. A hole 50a2 may be provided for inner ratchet bolt 50a. Inner collar support column 20a4 may include a female dovetail slot 20a4b that mates with a male dovetail slot on brace support 20a2, allowing brace support 20a2 to slide along support column 20a4 as inner ratchet bolt 50a is tightened. Hole 20a5a may be provided in outer collar support column 20a5 to allow outer ratchet bolt 50a1 to be tightened to then compress the riser pipe 1. Notice that alignment bolt tab 20a3b1 may be provided for alignment bolt 20a3b (shown in FIG. 6), to allow alignment bolt to hold brace support 20a3 (shown in FIG. 6) within the housing of outer collar support column 20a5. Male dovetail slot 20a5b may be provided on support column 20a5. The male dovetail slot 20a5b may mate with a female dovetail slot on the brace bracket 20a3, to allow brace bracket 20a3 to slide along support column 20a5 as ratchet bolt 50a1 (shown in FIG. 6) is tightened to compress riser pipe 1.

Figure 6B:
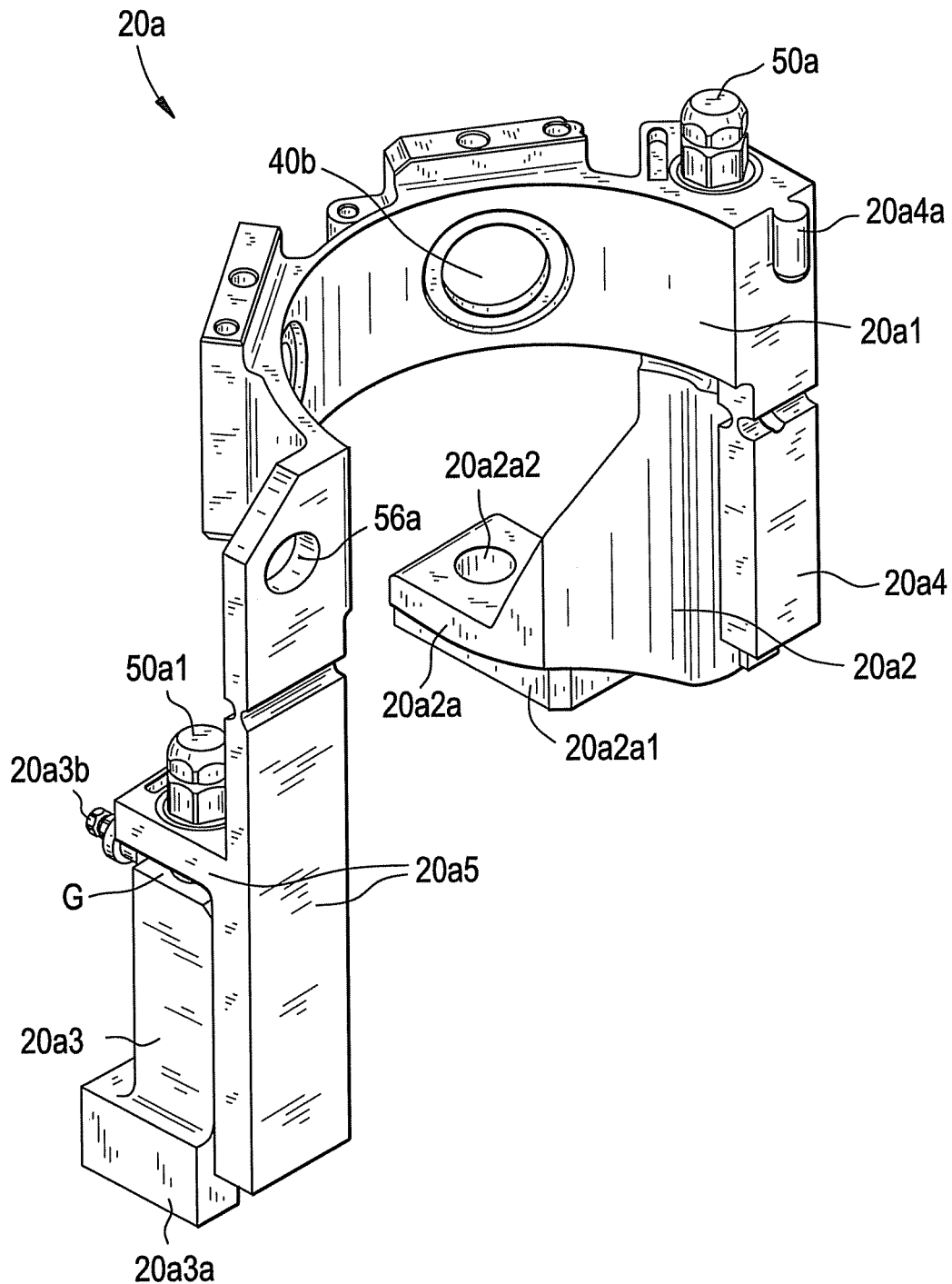
FIG. 6B is a detailed view of an upper collar assembly (right side) from a rear vantage point, in accordance with an example embodiment.

FIG. 6B is a detailed view of an upper collar assembly (right side) 20a from a rear vantage point, in accordance with an example embodiment. This figure shows the collar 20a from another vantage point. Note that gap G exists between outer collar support column 20a5 and the top of brace bracket 20a3. The gap G is reduced as outer ratchet bolt 50a1 is tightened when riser pipe 1 is put into compression. Male interlock 20a4a can be better seen in this drawing. Male interlock 20a4a mates with female slot 20a4b' to then interlock the inner ends of the upper collars 20a1/20a1' with each other.

Figure 7:
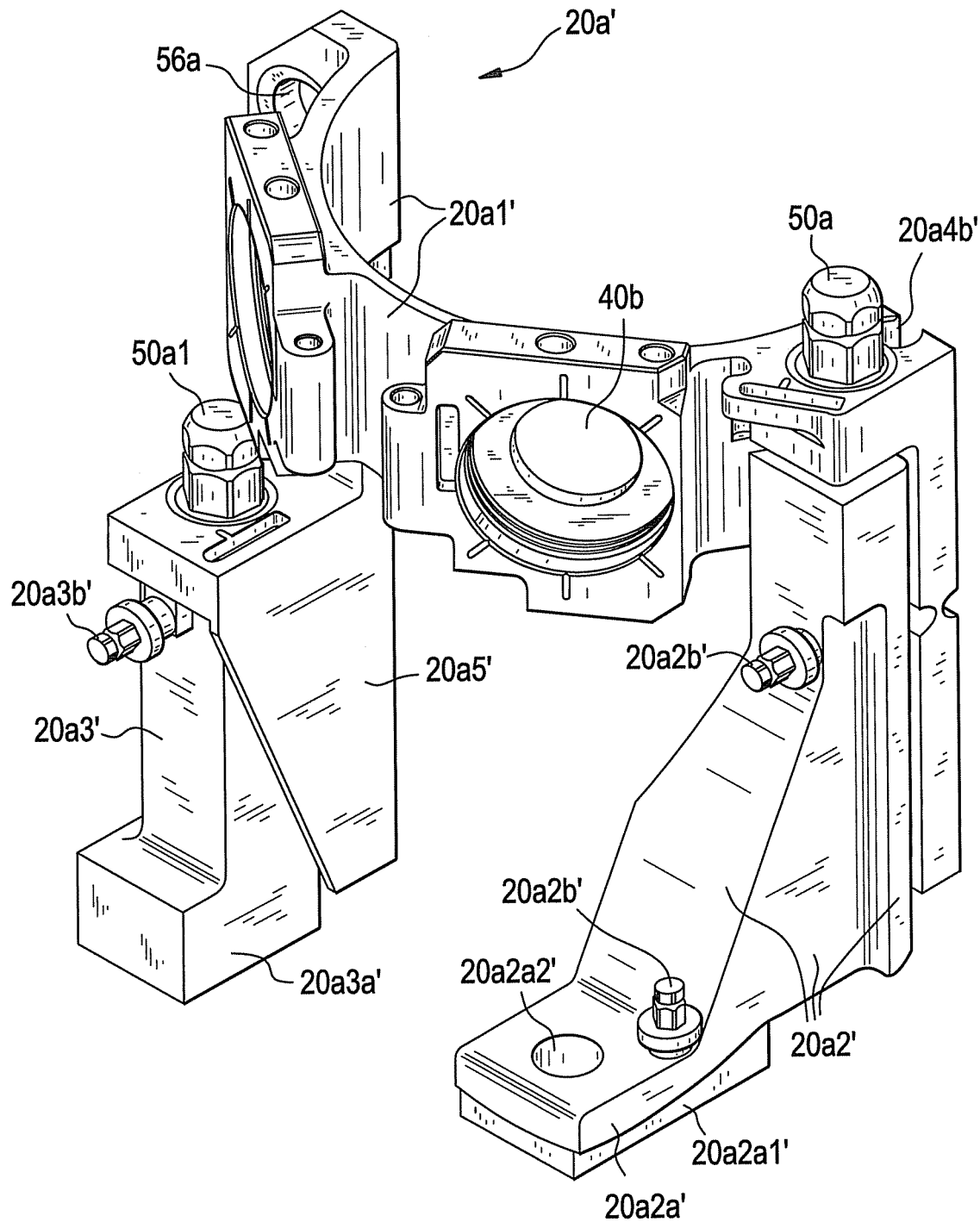
FIG. 7 is a detailed view of an upper collar assembly (left side), in accordance with an example embodiment.

FIG. 7 is a detailed view of an upper collar assembly (left side) 20a', in accordance with an example embodiment. The assembly 20a' may include a C-shaped half collar 20a1' with undersized collar holes 40b. Collar bolt hole 56a is provided to allow collar bolt to hold outer collar support columns 20a5/20a5' together (as shown in FIG. 5). Temporary alignment bolt 20a3b' may be provided to temporarily hold brace bracket 20a3' in the outer collar support column housing 20a5' prior to installation. Brace bracket foot 20a3a' may be connected to support column foot 20b5b' via ratchet bolt 50a1 (as shown in FIG. 5).

Female slot 20a4b' may be provided to interlock with male interlock 20a4a of upper collar assembly (left side) 20a'. Brace support 20a2' may be provided with a brace support foot (with convex spherical seat) 20a2a' that mates with the spherical (concave) seat of foot pad 20a2a1'. Temporary alignment bolts 20a2b' are provided to connect brace support 20a2' to foot pad 20a2a' and support column 20a4' prior to installation. Yoke bolt hole 20a2a2' is provided for yoke bolt 52 (as shown in FIG. 4).

Figure 7A:
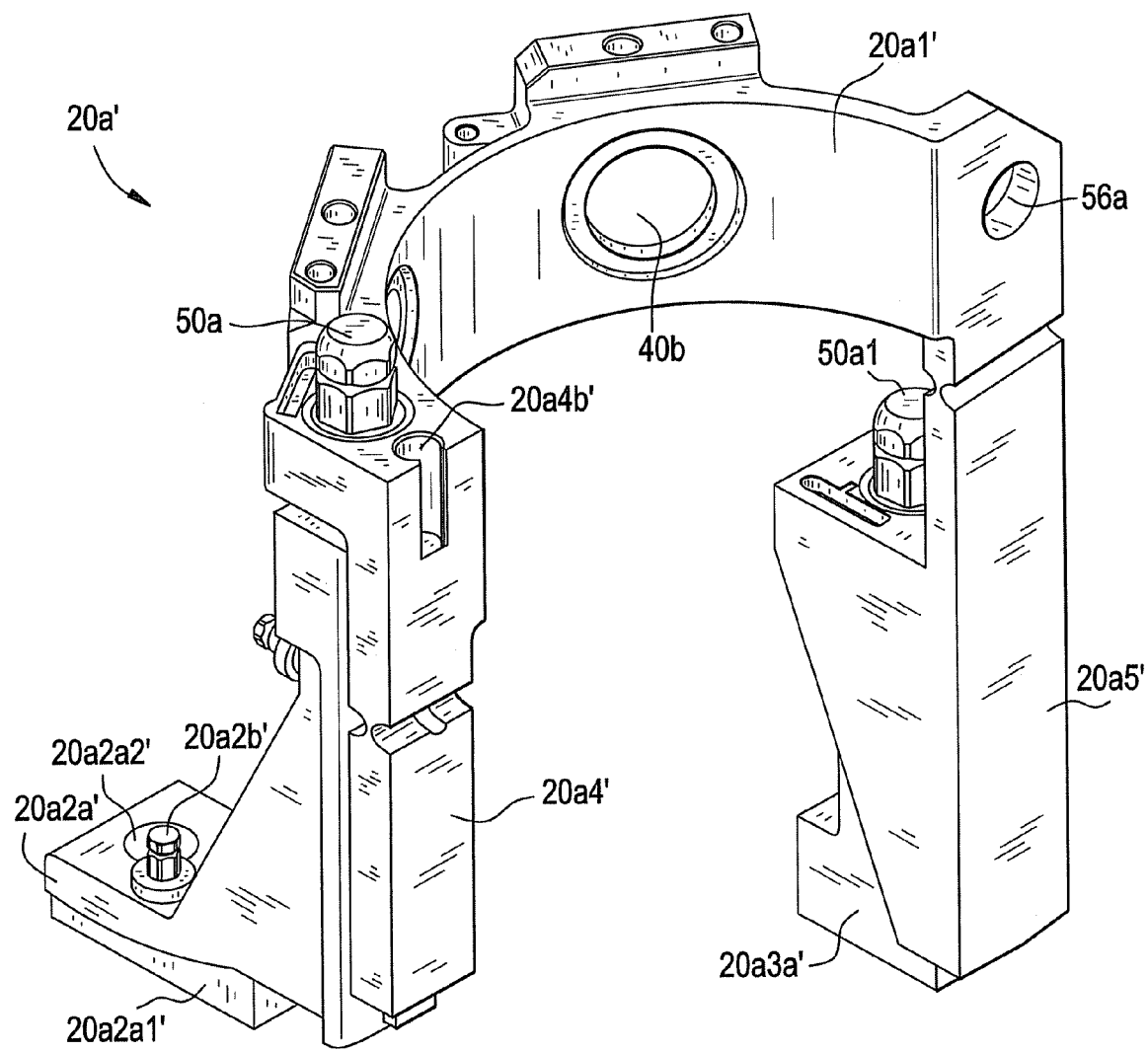
FIG. 7A is a detailed view of an upper collar assembly (left side) from a rear vantage point, in accordance with an example embodiment.

FIG. 7A is a detailed view of an upper collar assembly (left side) 20a' from a rear vantage point, in accordance with an example embodiment. All of the features shown in this drawing have been described in the description of FIG. 7, above.

Figure 7B:
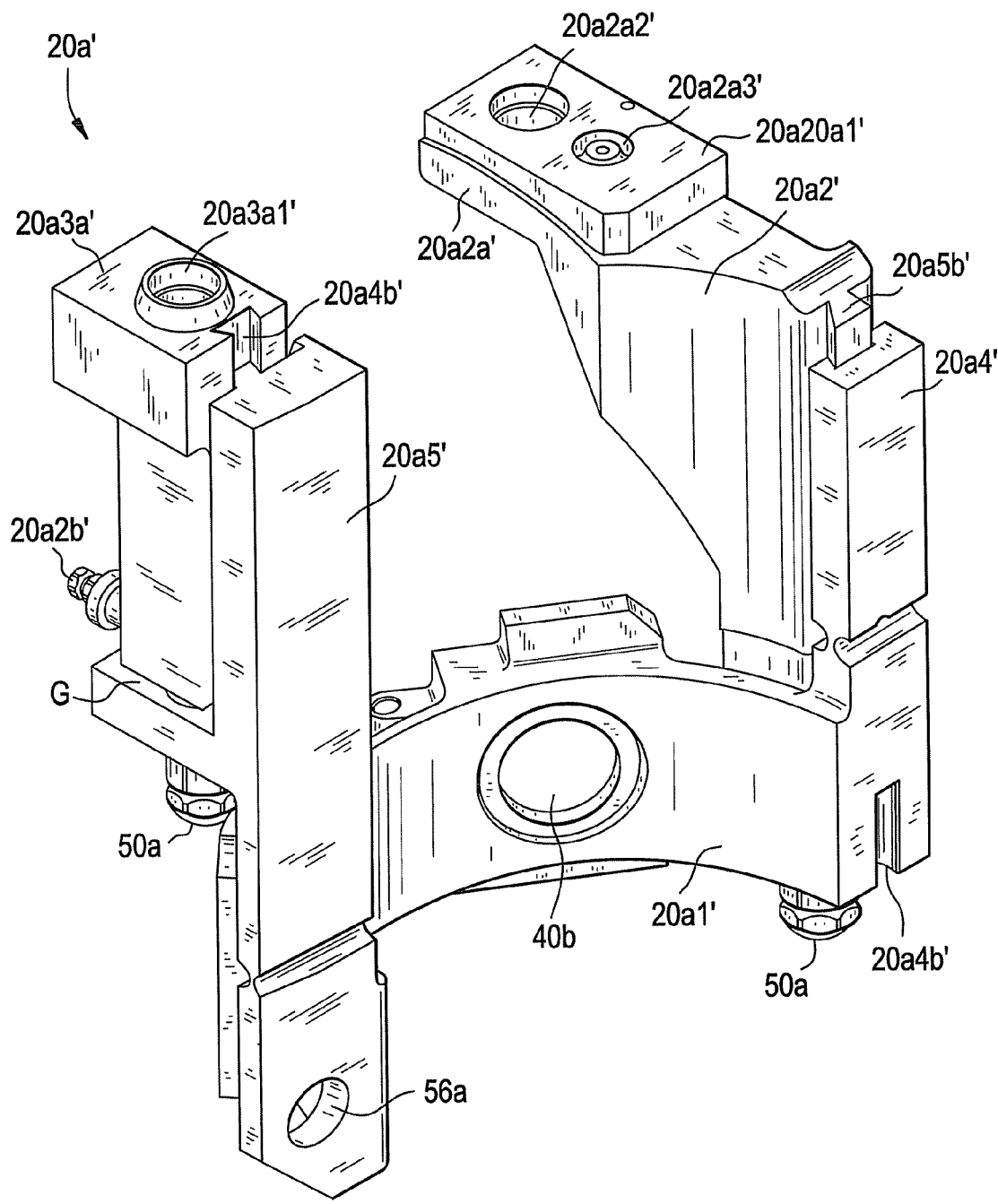
FIG. 7B is a detailed view of an upper collar assembly (left side) from a rear vantage point, in accordance with an example embodiment.

FIG. 7B is a detailed view of an upper collar assembly (left side) 20a' from a rear vantage point, in accordance with an example embodiment. Note that the bottom of foot pad 20a2a1' may include a recessed hole 20a2a3' for alignment bolt 20a2b'. A male dovetail boss 20a5b' may be provided on brace support 20a2' that mates with a female dovetail slot 20a4', allowing brace support 20a2' to slide along support column 20a4' as inner ratchet bolt is tightened to put the riser pipe 1 in compression. All other features of this drawing have been described for FIG. 7, above.

While example embodiments provide two separate upper collar assemblies 20a/20a', it should be understood that the two assemblies may instead be one single assembly or multiple assemblies. Likewise, the two separate lower collar assemblies 20b/20b' described below may also be one single assembly or multiple assemblies.

Figure 8:
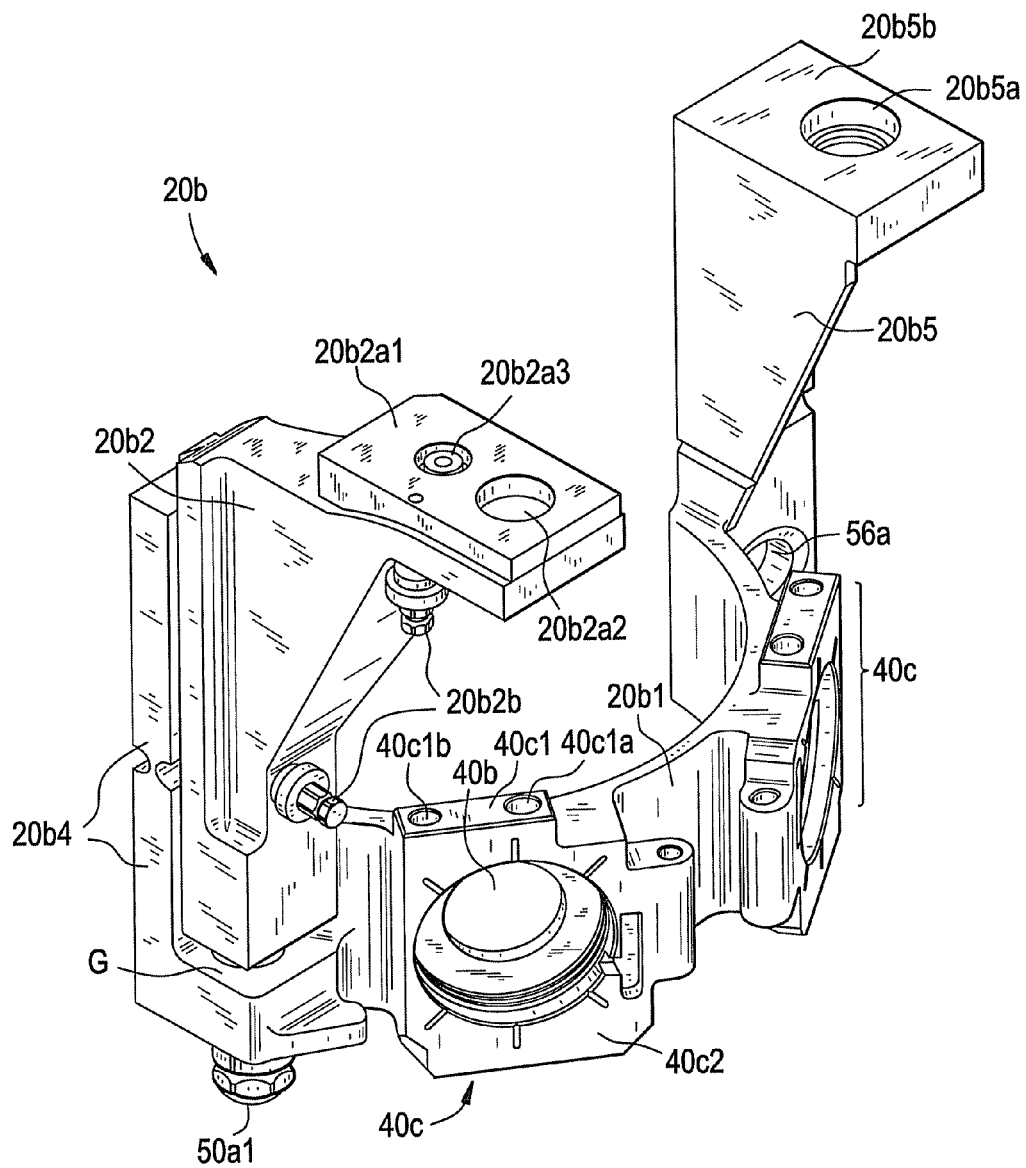
FIG. 8 is a detailed view of a lower collar assembly (right side), in accordance with an example embodiment.

FIG. 8 is a detailed view of a lower collar assembly (right side) 20b, in accordance with an example embodiment. Lower collar assembly 20b may include a C-shaped lower collar 20b 1. Brace support foot pads 20b2a1 may have a concave spherical shape mating with a convex spherical shape of the brace support seat 20b2a. A recessed hole 20b2a3 may be provided on the foot pad 20b2a1 for temporary alignment bolt 20b2b, as described in embodiments above. Hole 20b5a may be provided to secure support column foot 20b5b' to brace support foot 20a3a' using outer ratchet bolt 50a1, as shown in FIG. 5. Collar bolt hole 56a may be provided in outer collar support column 20b5 to connect support column 20b5 to support column 20b5', as shown in FIG. 5. The remaining features of this drawing are self-evident and have previously been described in example embodiments above.

Figure 8A:
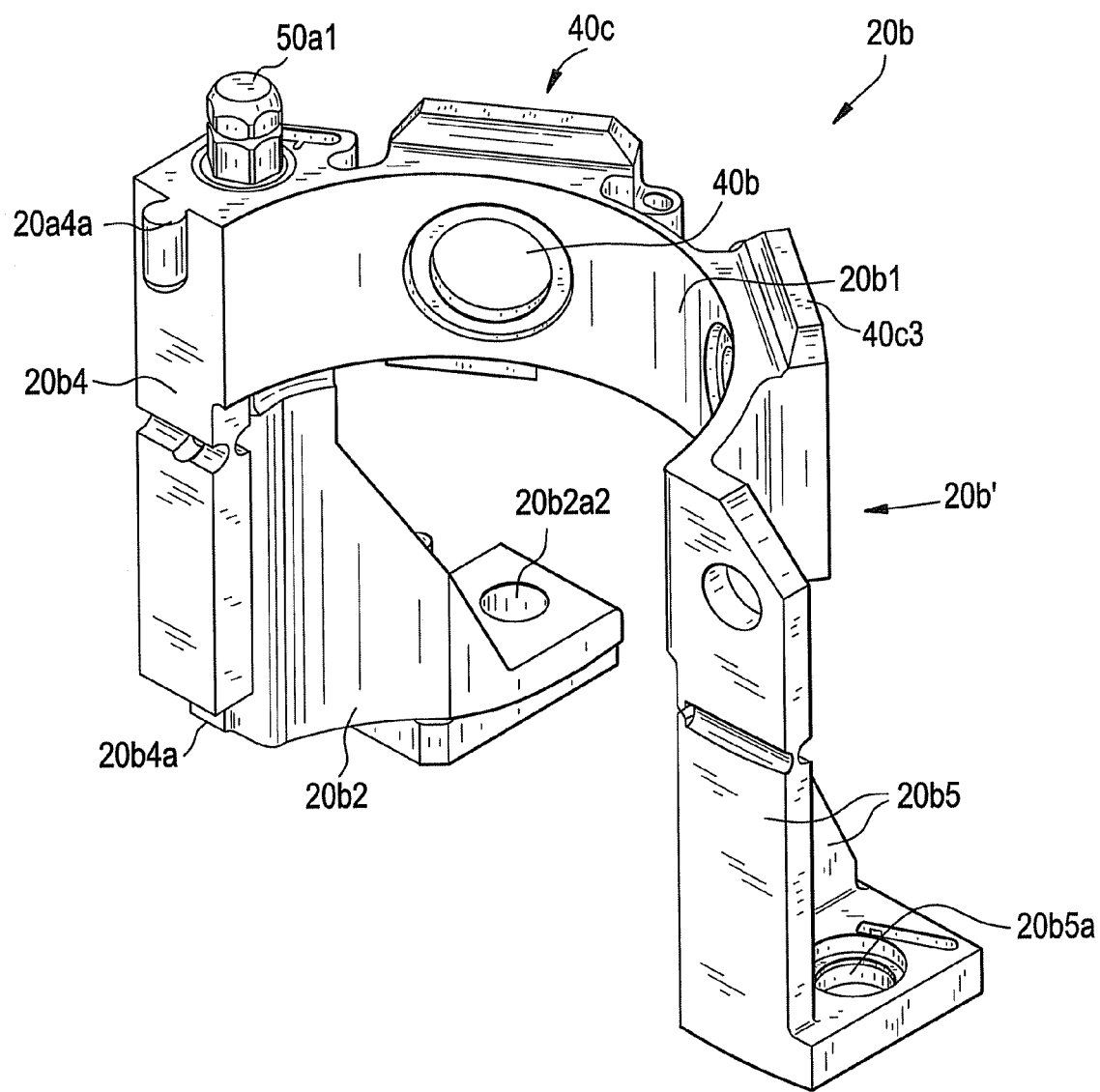
FIG. 8A is a detailed view of a lower collar assembly (right side) from a rear vantage point, in accordance with an example embodiment.

FIGS. 8 and 8A also show some features of the plug pad 40c, which may be common for all plug pads 40c of all collars. Specifically, a lower datum face 40c1 of plug pad 40c may include both an alignment slot 40c1a and a datum hole 40c1b, and a boss 40c3 with an angled surface may be provided on a top surface of the plug pad 40c. The alignment slot 40c1a, datum hole 40c1b and boss 40c3 may be provided for tooling purposes, to allow tools to grip and align with a front datum face 40c2 of the plug pad 40c. This ensures that match drilling of lower collar 20b 1 and riser pipe 1 may be accomplished to form an undersized collar hole 40b that is accurately aligned with a hole in the riser pipe, facilitating a tighter tolerance for plug assembly 40 to then fill collar hole 40b and the hole in the riser pipe 1.

FIG. 8A is a detailed view of a lower collar assembly (right side) 20b from a rear vantage point, in accordance with an example embodiment. Note the male interlock 20a4a that may be provided to mate with a female interlock 20b4b' of lower collar assembly 20b' (shown in FIG. 9A). A male dovetail 20b4a may be provided on brace support 20b2 that may mate with a female dovetail provided on the inner collar support column 20b4. The remaining features of this drawing are self-evident as they have previously been described in the embodiments above.

FIG. 9 is a detailed view of a lower collar assembly (left side) 20b', in accordance with an example embodiment. Lower collar assembly 20b' may include a C-shaped half collar 20b1'. Hole 20b5a' may be provided to connect outer collar support column foot 20b5b' to brace support foot 20a3a' via ratchet bolt 50a1, as shown in FIG. 5. Female dovetail slot 20b4b' may be provided to allow brace support 20b2' to slide along the surface of inner collar support column 20b4' (shown in FIG. 3, but not in this drawing) as inner ratchet bolts 50b are tightened. The remaining features of this embodiment are self-evident and have been described in previous embodiments of this disclosure.

Figure 9A:
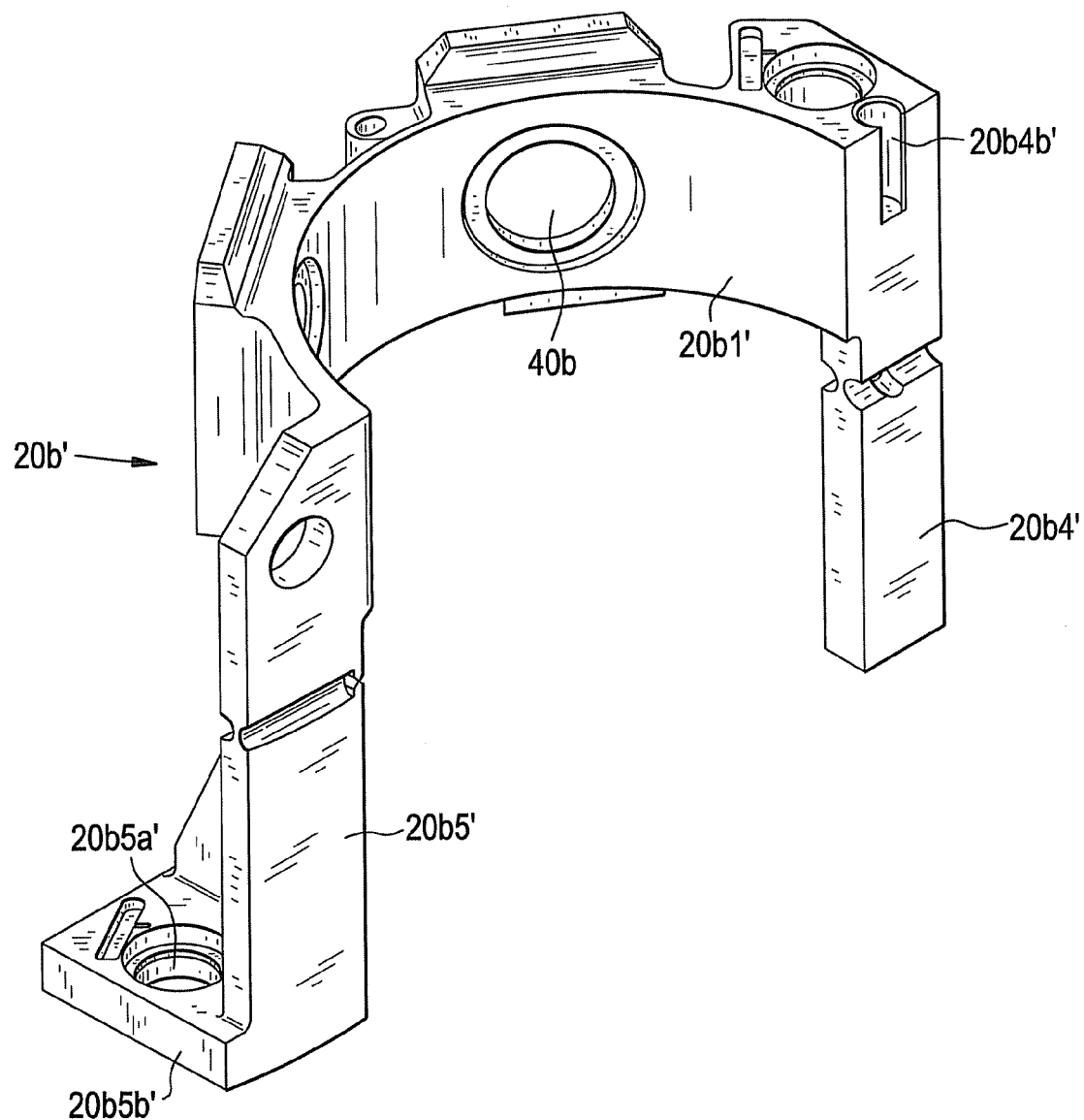
FIG. 9A is a detailed view of a lower collar assembly (left side) from a rear vantage point, in accordance with an example embodiment.

FIG. 9A is a detailed view of a lower collar assembly (left side) 20b', from a rear vantage point, in accordance with an example embodiment. Female interlock 20b4b' may be provided to interlock with male interlock 20a4a of lower collar assembly 20b (shown in FIG. 8). The remaining features of this drawing are self-evident and have been described in previous embodiments of this disclosure.

FIG. 10 is a detailed view of a clamp assembly (upper and lower clamp assemblies 30a/30b) installed above and below a riser brace 3 on a riser pipe 1, in accordance with an example embodiment. Upper clamp assembly 30a may include a C-shaped inner clamp 30a1 connected to another C-shaped outer clamp 30a4 (shown in FIG. 11). The inner/outer clamp portions 30a1/30a4 may be joined via mating fixtures 30a3. An alignment pin 30a5 may be provided to temporarily hold the inner/outer clamp portions 30a1/30a4 in place prior to being bolted together. Inner foot 30a2 and tooling tabs 30a3a may be provided to orient the inner/outer clamp portions 30a1/30a4 above the riser brace 3, although the upper clamp portions 30a1/30a4 are not directly connected to the riser brace 3 itself.

The lower clamp assemblies 30b1/30b4 (30b4 is shown in FIG. 10) similarly may be temporarily held in place via alignment pins 30b5 located in mating fixtures 30b3, prior to being bolted together. Inner foot 30b2 and tooling tabs 30b3b (shown in FIG. 11) may also be provided on the lower clamp assemblies 30b1/30b4, similar to the upper clamp assemblies.

Figure 11:
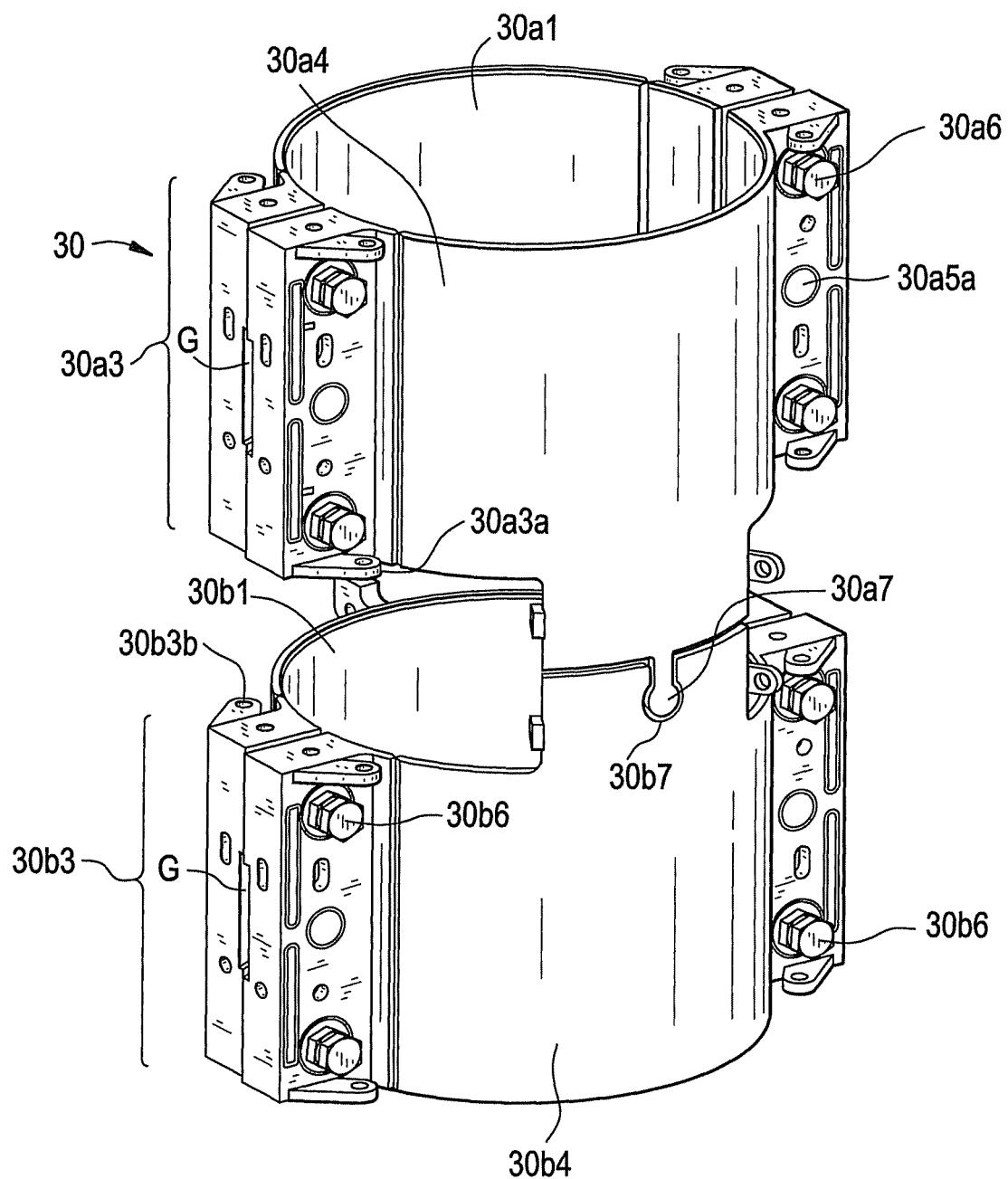
FIG. 11 is a detailed view of a clamp assembly (rear vantage point), in accordance with an example embodiment.

FIG. 11 is a detailed view of a clamp assembly (rear vantage point) 30, in accordance with an example embodiment. Clamp bolts 30a6 may be used to secure the inner/outer clamp assemblies 30a1/30a4 to each other. Tightening of bolts 30a6 cause gap G to narrow, as bolts 30a6 may cause hoop forces to be placed on riser pipe 1. Alignment pins 30a5 may then be removed from alignment pin hole 30a5a, once the inner/outer clamp assemblies 30a1/30a4 have been bolted into place on riser pipe 1.

Outer (upper) clamp 30a4 may have a male interlock 30a7 that mates with female interlock 30b7 of outer (lower) clamp 30b4. The lower clamp portions 30b1/30b4 may similarly be held together via clamp bolts 30b6 that cause gap G to narrow as clamp portions 30b1/30b4 may put hoop forces on riser pipe 1. The hoop forces may radially reinforce the integrity of the riser pipe 1 to relieve some of the radial pressure that is experienced by the riser pipe 1.

While example embodiments provide a clamp assembly with two separate upper clamps 30a1/30a4 (and two separate lower clamps 30b1/30b4), it should be understood that one circular upper clamp and one circular lower clamp may instead be used. Likewise, one overall clamp assembly may be used in lieu of separate upper and lower clamp assemblies. Furthermore, example embodiments provide a clamp assembly 30 separated from the riser pipe repair with compression 20. However, the clamp assembly 30 may instead be integral with the repair with compression 20.

Materials of construction for components of the above described example embodiments may include XM-19, preferably, or X-750 alternatively, for all alignment pins and bolts. All other components may be 304SS or 316SS (300-series, stainless steel), preferably, or XM-19, alternatively.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed is:

1. A riser pipe repair, comprising:
a first collar configured to attach to a straight portion of a riser pipe of a boiling water reactor (BWR) jet pump assembly;
one or more upper support columns attached to the first collar;
a second collar configured to attach to the straight portion of the riser pipe;
one or more lower support columns attached to the second collar;
brace supports slideably attached to the upper and lower support columns, the support columns and brace supports each having a longitudinal length that is configured to exist in a plane that is substantially parallel to a longitudinal length of the straight portion of the riser pipe; and
ratchet bolts connecting the brace supports to the upper and lower support columns, the brace supports, and the upper and lower support columns configured to axially compress the straight portion of the riser pipe by applying an axial compression force in a direction running along the longitudinal length of the straight portion of the riser pipe as the ratchet bolts are tightened.

2. The riser pipe repair of claim 1, wherein,
the upper support columns include a first and a second upper/inner support column and a first and a second upper/outer support column;
the lower support columns includes a first and a second lower/inner support column and a first and a second lower/outer support column;
the brace supports include an inner brace support for each of the inner support columns, the inner brace support being attachable to a riser yoke of a riser brace; and
the brace supports also include an upper/outer brace support for each of the first and second upper/outer support columns.

3. The riser pipe repair of claim 2, further comprising:
one or more collar holes in each of the first and second collars, each of the collar holes configured to accept an expandable plug to attach the collar to the riser Pipe;
wherein,
the first collar is attachable to the riser pipe above the riser brace,
the second collar is attachable to the riser pipe below the riser brace.

4. The riser pipe repair of claim 3, further comprising:
a clamp assembly attachable to an outer surface of the riser pipe between the first collar and the second collar on the riser pipe.

5. The riser pipe repair of claim 4, wherein,
the clamp assembly includes an upper and a lower clamp assembly,
the upper clamp assembly attachable to the riser pipe above the riser brace and including two C-shaped clamps, the lower clamp assembly attachable to the riser pipe below the riser brace and including two C-shaped clamps.

6. The riser pipe repair of claim 5, further comprising:
clamp bolts connecting respective ends of the upper and lower C-shaped clamps to each other;
gaps between the respective ends of the upper and lower C-shaped clamps, the C-shaped clamps configured to allow the gaps to narrow as the clamp bolts are tightened and hoop forces are placed on the riser pipe.

7. The riser pipe repair of claim 5, further comprising:
at least one interlock connecting the upper and lower clamp assemblies to each other.

8. The riser pipe repair of claim 2, wherein,
the ratchet bolts include a ratchet bolt for each brace support and support column pair,
the riser pipe repair defining a gap between a portion of each brace support and support column pair,
each brace support and support column pair configured to slide between each other allowing the gap to narrow as the ratchet bolts are tightened and the riser pipe is compressed.

9. The riser pipe repair of claim 8, further comprising:
male and female dovetail slots on contact surfaces between each brace support and support column pair.

10. The riser pipe repair of claim 8, further comprising:
brace support feet on an end of each of the upper/outer brace supports; and
support column feet on an end of each of the lower/outer support columns, the support column feet attached to the brace support feet via the ratchet bolts of the upper/outer brace support and support column pairs.

11. The riser pipe repair of claim 2, further comprising:
convex spherical bottom ends on each of the inner brace supports;
brace support foot pads attachable to the bottom end of each of the inner brace supports, each brace support foot pad having a concave shape configured to mate with the convex bottom end of the inner brace support to allow the brace support to pivot on the foot pad; and
yoke bolts configured to attach respective inner brace support and foot pad pairs to the riser brace yoke, a yoke bolt penetrating the bottom end of each inner brace support and foot pad.

12. The riser pipe repair of claim 1, wherein,
the first and second collars both include two C-shaped half collars joined together by mating male and female interlocks and collar bolts.

13. The riser pipe repair of claim 1, wherein the ratchet bolts have a longitudinal length that is about parallel to the longitudinal length of the straight portion of the riser pipe.

14. The riser pipe repair of claim 1, wherein,
the support columns and brace supports each have a longitudinal length that is about parallel to the longitudinal length of the straight portion of the riser pipe,
the brace supports are slideably attached to the upper and lower support columns, and the brace supports slide in a direction that is about parallel to the longitudinal length of the straight portion of the riser pipe.

15. The riser pipe repair of claim 1, wherein,
the first collar and the second collar exist in horizontal planes that are about parallel to each other,
the upper support columns vertically extend below and away from the first collar and toward the second collar,
the lower support columns vertically extend above and away from the second collar and toward the first collar.

16. The riser pipe repair of claim 1, wherein the upper and lower support columns that are configured to apply the compression force along the longitudinal length of the straight portion of the riser pipe do so by pulling the first collar and the second collar toward each other.

17. A riser pipe repair installed on a riser pipe, comprising:
a first collar attached to a straight portion of a riser pipe of a boiling water reactor (BWR) jet pump assembly above a riser brace;

a first and second upper/inner support column and a first and second upper/outer support column attached to the first collar;

a second collar attached to the straight portion of the riser pipe below the riser brace;

a first and second lower/inner support column and a second lower/outer support column attached to the second collar;

inner brace supports slideably attached to the inner support columns and the riser brace yoke, the inner brace supports being connected to the yoke via yoke bolts;

outer brace supports slideably attached to the upper/outer support columns and the lower/outer support columns;

ratchet bolts connecting the brace supports to each respective support column, the brace supports and respective support columns configured to axially compress the straight portion of the riser pipe by applying an axial compression force in a direction running along a longitudinal length of the straight portion of the riser pipe as the ratchet bolts are tightened.

18. The riser pipe repair of claim 17, wherein the ratchet bolts have a longitudinal length that is about parallel to the longitudinal length of the straight portion of the riser pipe.

19. The riser pipe repair of claim 17, wherein, the support columns and brace supports each have a longitudinal length that is about parallel to the longitudinal length of the straight portion of the riser pipe, the brace supports are slideably attached to the upper and lower support columns, and the brace supports slide in a direction that is about parallel to the longitudinal length of the straight portion of the riser pipe.

20. The riser pipe repair of claim 17, wherein, the first collar and the second collar exist in horizontal planes that are about parallel to each other, the upper support columns vertically extend below and away from the first collar and toward the second collar, the lower support columns vertically extend above and away from the second collar and toward the first collar.

21. The riser pipe repair of claim 17, wherein the upper and lower support columns that are configured to apply the compression force along the longitudinal length of the straight portion of the riser pipe do so by pulling the first collar and the second collar toward each other.

* * * * *